(12) United States Patent
Kirstgen et al.

(10) Patent No.: US 11,234,724 B2
(45) Date of Patent: Feb. 1, 2022

(54) SURGICAL INSTRUMENT WITH TWO-STAGE ACTUATION GEAR MECHANISM

(71) Applicant: Erbe Elektromedizin GmbH, Tübingen (DE)

(72) Inventors: Udo Kirstgen, Rottenburg (DE); Volker Buntrock, Reutlingen (DE)

(73) Assignee: Erbe Elektromedizin GmbH, Tübingen (DE)

( * ) Notice: Subject to any disclaimer, the term of this patent is extended or adjusted under 35 U.S.C. 154(b) by 399 days.

(21) Appl. No.: 16/028,702

(22) Filed: Jul. 6, 2018

(65) Prior Publication Data
US 2019/0008537 A1    Jan. 10, 2019

(30) Foreign Application Priority Data
Jul. 6, 2017    (EP) .................................... 17180062

(51) Int. Cl.
*A61B 17/29*    (2006.01)
*A61B 34/00*    (2016.01)
(Continued)

(52) U.S. Cl.
CPC ............ *A61B 17/29* (2013.01); *A61B 17/295* (2013.01); *A61B 17/2909* (2013.01);
(Continued)

(58) Field of Classification Search
CPC ... A61B 17/2909; A61B 17/29; A61B 17/295; A61B 2017/2923; A61B 2017/2913;
(Continued)

(56) References Cited

U.S. PATENT DOCUMENTS

| | | |
|---|---|---|
| 5,817,093 A | 10/1998 | Williamson, IV |
| 7,819,299 B2 | 10/2010 | Shelton, IV et al. |

(Continued)

FOREIGN PATENT DOCUMENTS

| | | |
|---|---|---|
| DE | 102010025550 A1 | 12/2011 |
| EP | 2000100 A2 | 12/2008 |

(Continued)

OTHER PUBLICATIONS

Extended European Search Report dated Nov. 16, 2017, for European Application No. 17180062.6 (6 pgs.).

(Continued)

*Primary Examiner* — Majid Jamialahmadi
(74) *Attorney, Agent, or Firm* — Fitch, Even, Tabin & Flannery LLP

(57) ABSTRACT

An instrument including an actuation gear mechanism that provides two functions of a tool. The actuation gear mechanism comprises a cam mechanism and a gear segment mechanism. The circumference of the cam disk of the cam mechanism—in a first section ($\alpha 1$)—is a spiral curve for generating a stroke for closing the forceps tool, while the circumference of the cam disk—in a second, adjoining, angular range ($\alpha 2$)—is circular. When the cam disk with the circular curved line biases the spring means, no further movement takes place on the output of the cam mechanism. Preferably, two congruent cam disks are provided, whereby these—together with the driving gear and the segment gear, as well as the shaft—form a one-piece plastic injection-molded part. The installation space between the cam disks can be utilized for a slide with a gear rack for shifting the knife.

14 Claims, 3 Drawing Sheets

(51) Int. Cl.
*A61B 17/295* (2006.01)
*A61B 17/00* (2006.01)
*A61B 18/14* (2006.01)
*A61B 17/32* (2006.01)
*A61B 18/00* (2006.01)

(52) U.S. Cl.
CPC .. *A61B 17/320016* (2013.01); *A61B 18/1445* (2013.01); *A61B 34/77* (2016.02); *A61B 2017/00367* (2013.01); *A61B 2017/2903* (2013.01); *A61B 2017/2915* (2013.01); *A61B 2017/2923* (2013.01); *A61B 2017/2925* (2013.01); *A61B 2018/0063* (2013.01); *A61B 2018/00404* (2013.01); *A61B 2018/00601* (2013.01); *A61B 2018/1455* (2013.01)

(58) Field of Classification Search
CPC .... A61B 2017/2925; A61B 2018/1455; A61B 2018/1452; A61B 34/77; A61B 18/1445
See application file for complete search history.

(56) References Cited

U.S. PATENT DOCUMENTS

| | | |
|---|---|---|
| 2013/0053831 A1 | 2/2013 | Johnson |
| 2015/0073394 A1* | 3/2015 | Schiele .............. A61B 18/1445 606/1 |
| 2017/0143361 A1* | 5/2017 | Boudreaux .......... A61B 17/295 |

FOREIGN PATENT DOCUMENTS

| | | |
|---|---|---|
| EP | 2845549 B1 | 8/2016 |
| JP | 2009-022742 A | 2/2009 |
| JP | 2015-054242 A | 3/2015 |
| SU | 733670 A1 | 5/1980 |

OTHER PUBLICATIONS

Russian Office Action dated Jun. 10, 2021, in corresponding Russian Application No. 2018123585/14(037404), with machine English translation (15 pages).

Japanese Office Action dated Oct. 14, 2021, in corresponding Japanese Application No. 2018-125690, with English translation (8 pages).

* cited by examiner

SURGICAL INSTRUMENT WITH TWO-STAGE ACTUATION GEAR MECHANISM

RELATED APPLICATION(S)

This application claims the benefit of European Patent Application No. 17180062.6, filed Jul. 6, 2017, the contents of which are incorporated herein by reference as if fully rewritten herein.

TECHNICAL FIELD

The invention relates to a surgical instrument for performing surgical procedures on a patient. In particular, this is an instrument whose tool comprises tool components that are to be activated in a chronologically offset manner, i.e., that are to be moved so as to achieve a desired surgical effect.

BACKGROUND

In principle, such an instrument has been known from publication EP 2 845 549 B1. It comprises a tool held on an elongated shaft, said tool comprising a forceps tool and a cutting tool. The forceps tool comprises two branches, at least one of which is supported so as to be movable, so that it is possible to grasp and compress tissue, for example a blood vessel or the like, between the branches. The branches bear electrodes for coagulating tissue and for fusing vessels. In contrast, the cutting tool is represented by a knife that can be moved in linear direction and has a cutting edge on its face side, and that—with the branches closed—can be moved in a cutting manner through the grasped and compressed vessel in order to sever said vessel.

In order to actuate the two tool parts, a housing with a hand lever is provided on the proximal end of the shaft. The housing accommodates an actuation gear mechanism that translates the movement of the hand lever into a pulling motion for closing the forceps tool and into a subsequently occurring pushing motion for the distal movement of the cutting tool. The actuation gear mechanism comprises a link drive for closing the forceps tool. The link drive comprises a connecting link that is connected to the hand lever in a hinged manner. If said hand lever is pivoted, the connecting link of the link drive is also pivoted, as a result of which a slide block is moved in proximal direction in order to close the forceps tool via a pulling means. The cutting tool is actuated via a slide connected to a gear rack that meshes with a gear that is rotatably held on the hand lever. On the opposite side of the gear, it meshes with a stationary toothing applied in the housing. As long as the link drive is active, the movement of the slide provided for actuating the knife is blocked. As soon as the connecting link has completed its movement, the movement of the slide in distal direction is cleared. The movement of the slide is effected by the gear supported on the end of the hand lever due to the linear movement caused by the hand lever. The prevention of the actuation of the knife, i.e., the linear movement of the gear for the first part of the movement of the hand lever requires a blocking device whose position and design must be carefully adapted to all other components. Furthermore, a relatively long path of the hand lever for closing the forceps tool and a relatively short operating path for the actuation of the cutting tool are the result.

Therefore, the object sought is a concept with which the operating paths for the two movable tool parts can be easily adapted to each other.

SUMMARY

This object is achieved with the instrument described herein.

The instrument according to one form of the invention may be configured as a laparoscopic instrument and, to do so, have a relatively stiff, thin, and long shaft that bears a tool on its distal end. In principle, the instrument comprising the features according to the invention may also be configured as an instrument for open surgical procedures or as an instrument for endoscopic applications.

Independent thereof, the instrument comprises an actuation gear mechanism for moving the two tool parts, in which case the actuation gear mechanism comprises a cam mechanism, as well as a gear segment mechanism. Preferably, the cam mechanism is disposed to generate a proximally directed driving movement, while the gear segment mechanism preferably is disposed for generating a distally directed driving movement. The cam disk has a peripheral surface that comes into contact with a cam follower, e.g., a roll, a sliding body, a lever or the like. Preferably, the cam follower can be moved in a direction radial with respect to the cam disk, as a result of which its direction of movement intersects the axis of rotation of the cam disk. Preferably, the radial direction of movement of the cam follower corresponds to the direction of movement of the pulling means for driving the first tool part. In order to effect a movement of the cam follower during the rotation of the cam disk, said disk has a section in which the radius of the peripheral surface increases or decreases as a function of the angle of rotation of the cam disk. To accomplish this, the axis of rotation of the cam disk is preferably located on the center axis of the shaft. As a result of this, no torque is applied to the cam disk by the cam follower, as soon as said cam follower has reached the cam disk section having the constant radius.

The two driving movements that are directed in opposite directions and can be sampled at both outputs of the actuation gear mechanism occur preferably chronologically offset, i.e., chronologically overlapping or not overlapping, in any event, in sequence, when the actuation gear mechanism is moved. To do so, preferably a manual actuation arrangement is used, said manual actuation arrangement being disposed to effect a rotation of both a cam disk belonging to the cam mechanism and also a preferably simultaneous rotation of a segment gear belonging to the gear segment mechanism. The manual actuation arrangement may be, e.g., a hand lever that is pivotally supported by the housing.

The forceps tool comprises at least one movable tool part such as, for example, a movable branch. It is also possible for both branches of the forceps tool to be movable, e.g., pivotable toward or away from each other. The movement of one or both movable tool parts of the forceps tool is transmitted from the actuation gear mechanism via a pulling means to the one or more movable tool parts of the forceps tool. The pulling means may be a plastic or metal wire, a plastic or metal ribbon, a plastic or metal cord or the like and extends preferably from the proximal end of the shaft, i.e., from the first output of the actuation gear mechanism up to the first movable tool part to which it is connected in a driving manner.

The cutting tool comprises at least one movably held knife that represents the second tool part. Preferably, the knife is a sliding knife that is moved in distal direction for the severing of tissue. For this, the second output of the actuation gear mechanism is connected—via a transmission means—to the knife, i.e., to the second tool part. The transmission means extends from the second output of the actuation gear mechanism in the vicinity of the proximal end of the shaft and then through the shaft up to the distal end thereof, and adjoins the second tool part there. The transmission means is preferably a pushing means that transmits a distally directed driving motion of the second output. The pushing means may be a rod, a tube or another flexurally rigid means that transmits pushing forces. Alternatively, the pushing means may also be a non-rigid means such as, e.g., a plastic or metal ribbon, that is guided laterally in a narrow channel so that it can only be moved in axial direction, but cannot evade in lateral direction.

Preferably, the segment gear and the cam disk are connected to each other in a torque-proof manner, in which case the segment gear comes into engagement with the gear rack only when the cam disk has moved a cam follower—for the actuation of the first tool part—completely or almost completely into a position in which the forceps tool is closed. Within this meaning, the gear rack and the segment gear form a positive locking coupling arrangement that connects and disconnects, i.e., couples and uncouples, a driving connection between the manual actuation arrangement and the second output at a specified location of the operating path of the manual actuation arrangement.

The cam disk has at least one ascending section having a radius that is a function of an angle and a second section in which the radius of the cam disk remains constant, independent of the angle of rotation, or in which case said radius even decreases slightly when the actuation direction is moved further. The section having the radius that is a function of the angle may be a spiral arch. The section in which the radius of the cam disk is constant irrespective of the angle of rotation, may be a circular arc that is concentric relative to the axis of rotation. Due to the angle-type adaptation of the transition between ascending and non-ascending section onto the segment gear, and the coupling location specified thereby, respectively, a desired coordination of the two movements of the tool parts relative to each other can be accomplished. For example, the movements of the two tool parts in succession with an interposed pause, a subsequent transition without pause, or an overlapping transition may be specified.

Preferably, the coupling location at which the toothing of the segment gear comes into engagement with the gear rack is located in a position of rotation in which the ascending section of the cam disk transitions into the non-ascending section. Furthermore, additional degrees of freedom of design exist, whereby these can be utilized independent of each other in order to adapt the lengths of the path sections of the actuation path of the manual actuation arrangement to the desired movements of the tool parts. Such a parameter, for example, is the diameter of the segment gear as well as the pitch of the radius on the cam disk.

Overall, simple kinematics are attained, which, in addition, will work with low actuation forces. The transition between the movement of the two tool parts may be a sliding movement and thus be accomplished without any related cracking or clicking noise, or the like, that is found to be irritating by the surgeon. Furthermore, it is possible to design the manual actuation arrangement as a pivoting lever that displays a fixed, unchangeable pivoting center. The pivoting center of the pivoting lever is the same for closing the forceps tool and for actuating the cutting tool. Furthermore, the requirements for manufacturing tolerances are only minimal in the case of the inventive actuation gear mechanism, which increases production reliability and actuation quality.

The actuation gear mechanism is preferably driven via a step-up gear that effects a small pivoting angle of the pivoted lever disposed for the manual actuation into a rotation of the cam disk and the curved gear by a greater angle of rotation. Such a step-up gear may be a pulling means gear, in which case a pulling means is connected to one end of a hand lever, and the other end is wound onto a winding member, e.g., a rope pulley, from where it is pulled off when the hand lever is actuated. In particular, however, the transmission gear may be a curved gear, and a gear or gear rack, meshing therewith, wherein the curved gear is connected to the pivot lever. The gear drives the segment gear and the cam disk.

Instead of the segment gear, an arcuate gear rack may be used, said gear rack being, e.g., rigidly, connected to the hand lever. Furthermore, the gear rack may also be straight and pivotally connect to the hand lever on one end. If the manual actuation arrangement is supported so as to be movable linearly, instead of pivotally, on or in the housing, the straight gear rack may also be rigidly connected to the manual actuation arrangement. In the simplest case, the cam disk, the segment gear and the gear used for driving can be connected to each other so as to form one piece. For example, they may be configured as a plastic injection-molded part or, in another way, as a seamless part of a uniform material.

BRIEF DESCRIPTION OF THE DRAWINGS

Additional details of advantageous embodiments of the invention can be inferred from the claims, the description or the drawings. They show in FIG. 1, a schematized side view of the instrument, FIG. 2, a partially greatly schematized basic diagram of the actuation gear mechanism, FIG. 3, a schematized plan view of the actuation gear mechanism according to FIG. 2, FIG. 4, a diagram to illustrate the operation of the actuation gear mechanism according to FIGS. 2 and 3, and FIG. 5, a diagram to illustrate a modified embodiment of the actuation gear mechanism.

DETAILED DESCRIPTION

Figure 1:
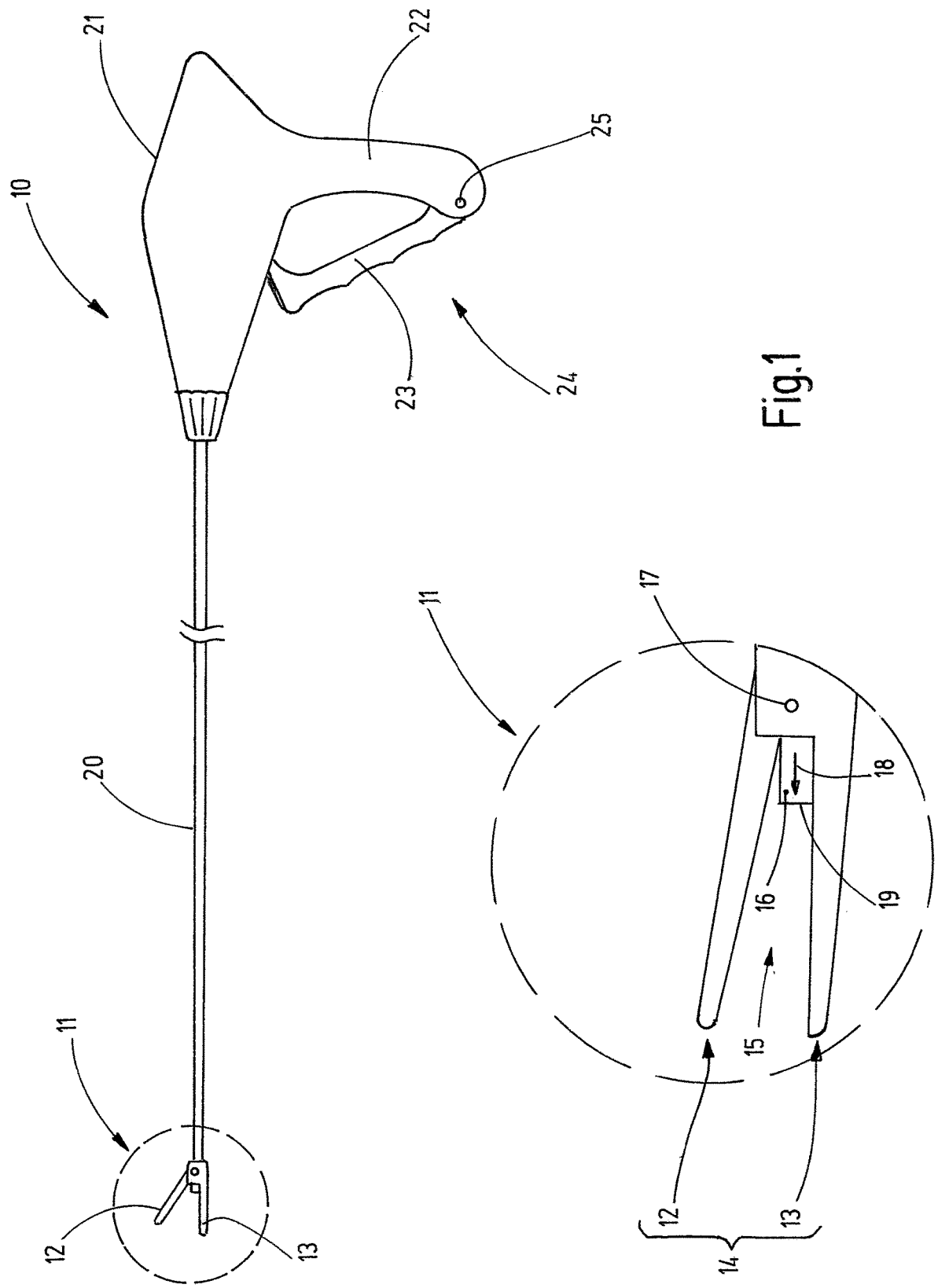

FIG. 1 shows a surgical instrument 10 that, as depicted, is intended for laparoscopic applications. The tool 11 is disposed for acting on biological material, in particular for acting on hollow vessels in a manner that they can be sealed and, optionally, severed. As can be inferred from the partial illustration in FIG. 1, bottom, the tool 11 comprises a forceps tool 14 having two branches 12, 13, as well as a cutting tool 15 that is formed by a knife 16 that is supported so as to be linearly movable.

Of these two branches 12, 13, at least one—branch 12 in FIG. 1—is supported so as to be pivotable about a hinge pin 17 and thus form a first movable tool part of the tool 11. The knife 16 of the cutting device 15 forms a second movable tool part. In the present exemplary embodiment, the knife 16, when activated, can be moved in distal direction in the direction indicated by arrow 18 for severing tissue. In doing so, the knife 16 moves in a recess or groove provided in the lower branch 14. Likewise, a corresponding recess or groove may be provided in the upper branch 12 in order to be able to move the knife 16 when the forceps tool 14 is closed. In doing so, a front cutting edge 19 penetrates tissue grasped between the branches 12, 13.

Not further illustrated means for acting on biological tissue such as, for example, electrodes, projections, teeth, recesses, edges or the like may be provided on the branches 12, 13, for example to be able to coagulate tissue grasped between the branches 12, 13 or to fuse vessels. The knife 16 may be a mechanical knife with a sharp cutting edge 19 or also an electrically cutting or electrically aided cutting knife, to which an appropriate electrical voltage can be applied for severing tissue by mechanical movable means and/or by aiding or affecting the cutting process.

The tool 11 is mounted to the distal end of an elongated shaft 20 whose proximal end is connected to a housing 21. The latter comprises a handle 22 that also includes a hand lever 23. Said hand lever represents a manual actuation arrangement 24. The hand lever 23 is supported at a suitable location of the housing 21, for example at a lower end of the handle 22 at a bearing point 25 in a movable manner, preferably in a pivotable manner.

Figure 2:
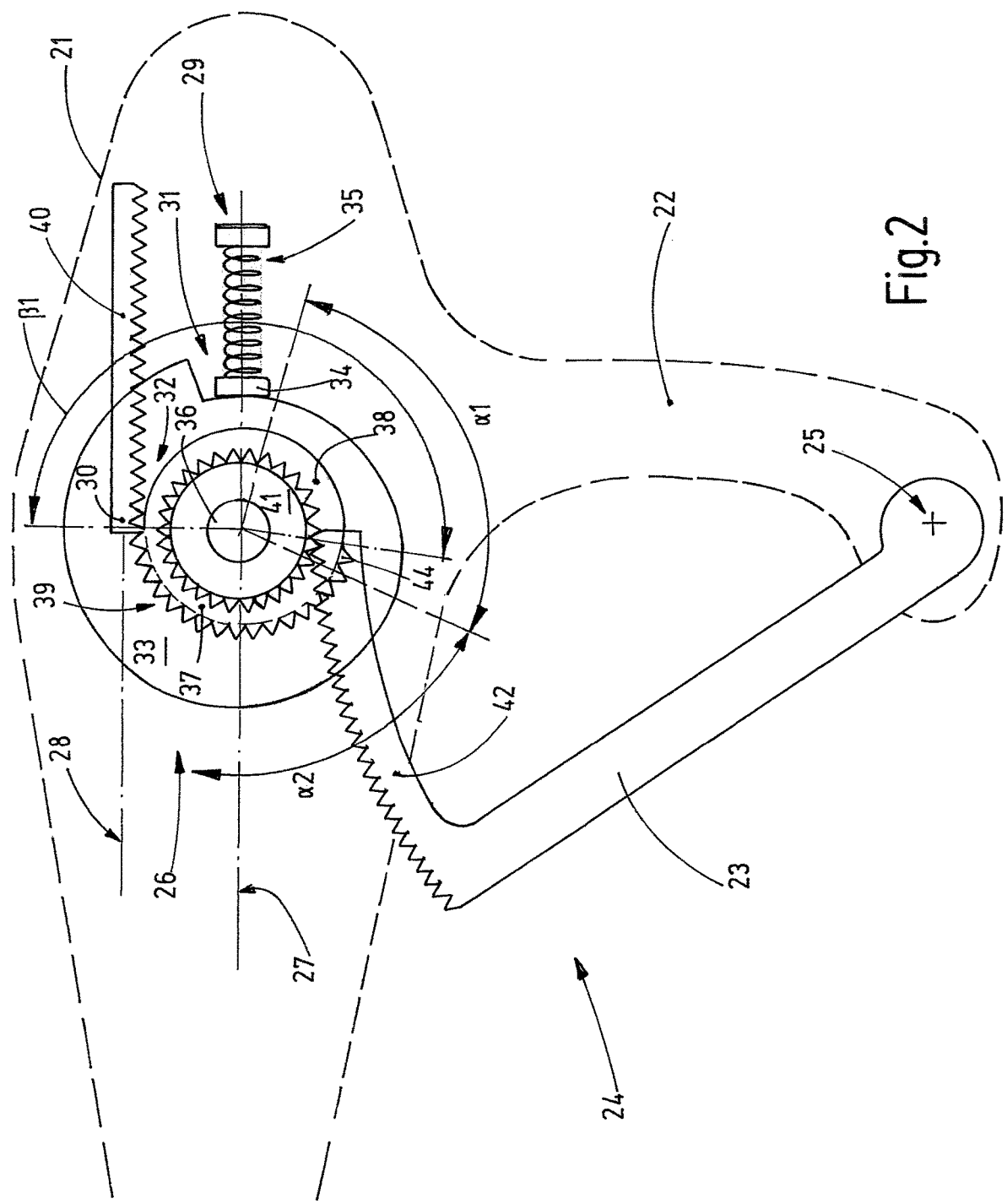

The housing 21 encloses an actuation gear mechanism 26 for the coordinated actuation of the movable tool parts 12, 16 of the tool 11 as illustrated by FIG. 2. In doing so, the actuation gear mechanism 26 converts the pivoting movement of the hand lever 23 into a coordinated push/pull movement of a pulling means 27 and a pushing means 28 that are connected—on their respective distal end—to the movable tool parts 12, 16 and—on their respective proximal end—to a first output 29 or the second drive 30 of the actuation gear mechanism. The first actuation means 27 is a pulling means such as, for example, a wire, a cord, a ribbon or the like of metal or a plastic material. It may be non-rigid or, alternatively, also rigid. In any event, it displays tensile strength relative to the essentially rigid transmission of a pulling movement by the first output 29 to the first tool part 12. If needed, the pulling means 27 may also be slightly elastic in longitudinal direction.

The pushing means 28 is disposed for the actuation of the cutting tool 15 and thus for the distal movement of the knife 16. While the distal end of the pushing means 18 is connected to the knife 16, its proximal end is connected to the second output 30 of the actuation gear mechanism 26. The pushing means 28 is preferably shear-resistant and, to do so, is configured as a tube or profile rod having a round profile, a rectangular profile as a solid or hollow profile, a U-profile or the like. The pushing means 28 may also a non-rigid element such as, for example, a plastic or steel ribbon that is guided in an appropriate channel. Alternatively, the pushing means 28 may be a minimally rigid plastic or metal profile, for example a U-profile whose lateral breakout is prevented in that said profile is guided, e.g., on a rib, in longitudinal direction through the shaft.

The actuation gear mechanism 26 comprises a cam mechanism 31 that comprises the first output 29, as well as a gear segment mechanism 32 that is associated with the second output 30.

The cam mechanism 31 comprises a cam disk 33 and a cam follower member 34, for example in the configuration of a sliding element, a roll or the like, which moves or move along the circumference of the cam disk 33. To do so, the cam follower member 34 is supported so as to be movable linearly in longitudinal direction of the pulling means 27 and radially movable with respect to the cam disk 33 and pushed by means of a spring means 35 effective between the first output 29 and the cam follower member 34—for example in the configuration of a helical spring—against the circumference of the cam disk 33. Instead of the spring means 35, it is also possible to provide a rigid connection between the cam follower member 34 and the first output 29, if the pulling means 27 is resilient in longitudinal direction and, to this extent, acts as a pulling spring. In other cases, a spring means may also be omitted altogether.

Figure 4:
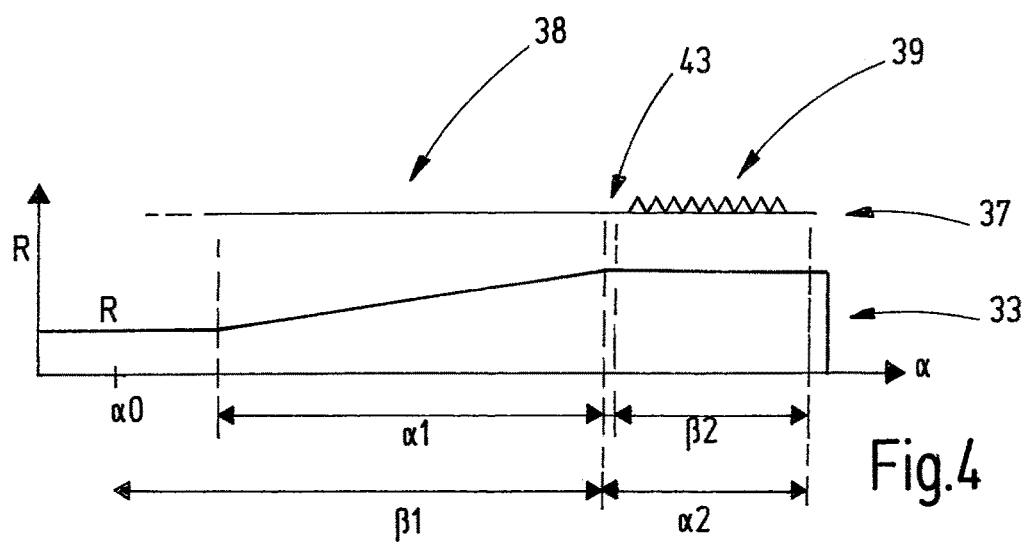

The circumference of the cam disk 33 has a first angle section α1, in which the radius increases in the event of a rotation of the cam disk 33 in the direction of actuation (in FIG. 2, a counterclockwise rotation). The angle section α1 is adjoined by an angular range α2, in which the radius of the cam disk 33 is independent of the angle. FIG. 4 illustrates the increase of the radius R in the angle section α1 and the constancy of the radius R in the angle section α2 in a Cartesian Diagram that may be understood as the windup of the cam disk 33.

Figure 3:
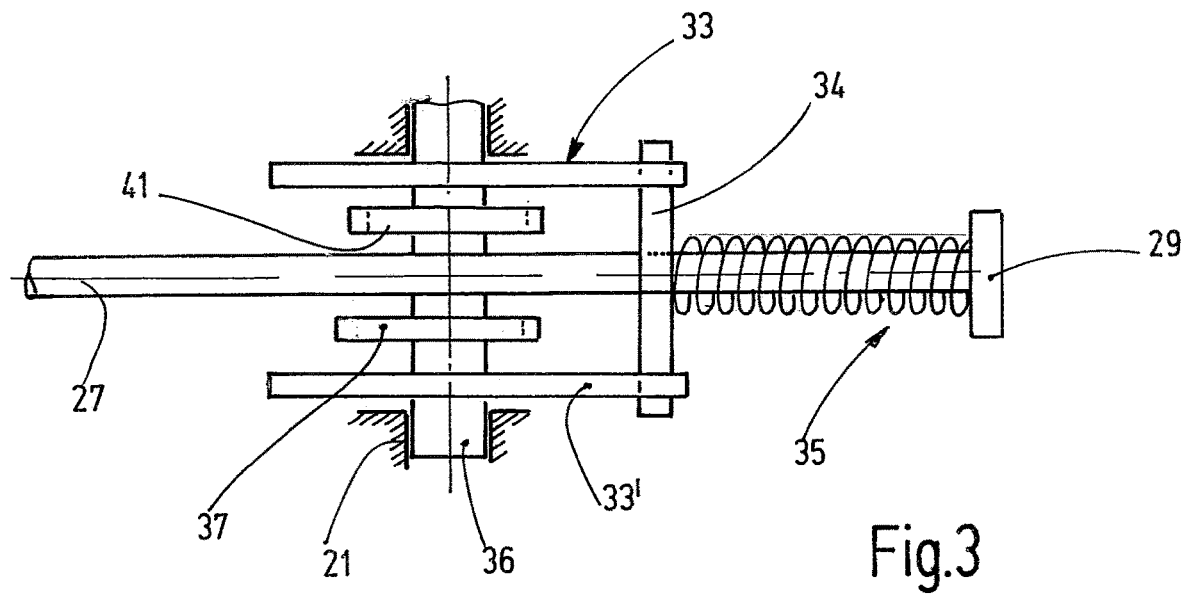

The cam disk 33 is rotatably supported on a shaft 36 in the housing 21 as is obvious from FIG. 3, in which case this shaft 36 may bear a second congruent cam disk 33' that also is in contact with the cam follower member 34, so that the latter can be moved linearly by the two synchronously rotating cam disks 33, 33'. In FIG. 2, the pulling means 27 is only shown by a chain line to indicate its direction of action. It may have an offset, a recess or the like in order to be guided around the shaft 36, as is obvious from FIG. 3.

Connected to the one or more cam disks 33, 33a in a torque-proof manner, there is a segment gear 37 belonging to the gear segment mechanism 32, said segment gear having a toothless section 38 and a section 39 that is provided with teeth. In FIG. 4, the segment gear 37 is depicted above the windup of the cam disk 33 as a windup as well. As is obvious, the sections 38, 39 are arranged, at least in one preferred embodiment, in such a manner that the toothless section 38 and the first angle section α1 of the cam disk 33 are functionally overlapping. For explanation, reference is again made to FIG. 2 that shows a gear rack 40 associated with the gear segment mechanism 32, said gear rack being supported in the housing 21 so as to be linearly movable in the direction of the pushing means 28. The gear rack 40 may be supported on a slide that, at the same time, forms the second output 30 or it may itself act as such an output. The toothless section 38 of the segment gear 37 takes up an angular range (31 that does not allow any driving connection between the segment gear 37 and the gear rack 40. While the toothless section 38 in FIG. 4 is shown in agreement with the ascending angle section α1 of the cam disk 33, the real angular offset between these sections is illustrated by FIG. 2. The reason for this is that, in the real embodiment according to FIG. 2, the cam follower member 34 and the gear rack start of the gear rack 40—viewed from the shaft 36—are angularly offset relative to each other, so that the gear segment mechanism 32 and the cam mechanism 31 have different zero points. These zero points are brought to coincide in FIG. 4. Thus, it can also be seen that the toothed section 39 of the segment gear 37 is active within an angular range (32, i.e., couples with the gear rack 40, in which the cam follower member 34 moves over the second angular range α2 of the cam disk 33.

Another gear 41 that couples with a gear segment 42 is disposed for the rotating drive of the cam disk 33 (and 33'), as well as the segment gear 37. The gear segment 42 is connected to the hand lever 23 that, for example, can be pivoted back and forth relative to the handle 22, against the force of a not specifically illustrated spring. In doing so, the gear segment 42 rotates the gear 41 and, with said gear, also the cam disk 33, as well as the segment gear 37.

The instrument 10 described so far operates as follows:
When initially used, the instrument 10 is in the position as shown by FIG. 1. The forceps tool 14 is open and the cutting tool 15 is inactive, i.e., the knife 16 is in proximal, retracted position. The hand lever 23 is in a starting position similar to FIGS. 1 and 2, in which one end of the gear segment 42 is out of engagement with the gear rack 40, and the cam follower member 34 is in a position of the cam disk 33, in which the cam disk 33 displays a minimal radius R. In FIG. 4, this corresponds to a rotational position α0 for the shaft 36 and for cam disks 33, 33' and the gears 37, 41 that are integrally connected to said shaft.

If the hand lever 23 is now pivoted toward the handle 22, the shaft 36 will rotate, as a result of which the cam follower member 34 slides along the first angle section α1 of the cam disk 33 and thus moves in proximal direction. This movement is transmitted via the spring means 35, or another connection, to the first output 29, so that the pulling means 27 is moved in proximal direction and thus the forceps tool 14 is closed. The full closure is preferably reached before the cam disk 33 has completely performed the rotation within the first angle section α1, so that the spring means 35 is tensioned (compressed) at the transition 43 between the angle section α1 and the angle range α2.

In the transition section 43, the curvature may gradually transition from the spiral form of the section α1 to the circular arc form of the angular region α2 that is concentric to the shaft 36. In or after the transition, the segment gear 37 and the gear rack 40 couple with each other. In doing so, the first tooth 44 of the section 39 meshes with the gear rack 40, so that a further rotation of the shaft 36 now effects a distal shift of the rack 40. This distal shift is transmitted via the pushing means 28 to the knife 16, i.e., to the cutting tool 15, so that biological material, for example a vessel, held between the two branches 12, 13 is severed.

It is understood that suitable inhibiting or blocking means may be provided in order to initially block a rotation of the shaft 36 after it has reached the transition section 43, in order to, for example, be able to effect a coagulation of the vessel or any other material between the branches 12 and 13 when the forceps tool 14 is closed. Appropriate blocking means for a temporary blocking of further movement, activation means for coagulation electrodes and other electrodes, switches and the like, are not shown in FIG. 2; however, the may be provided as needed.

Figure 5:
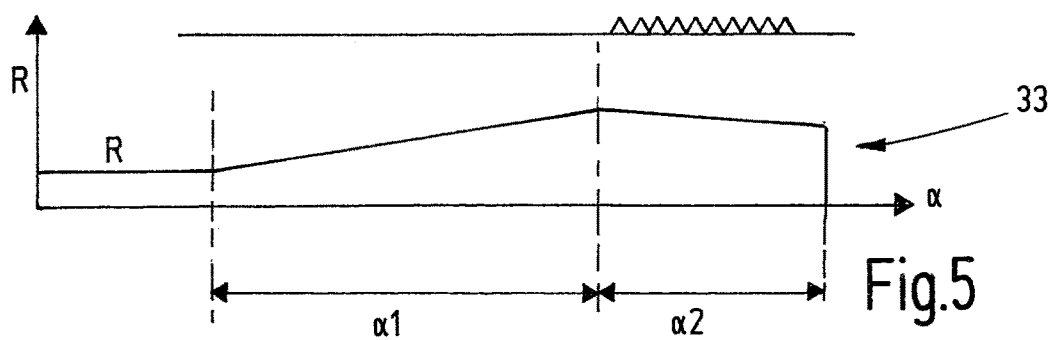

FIG. 5 shows a slightly modified embodiment of the actuation gear mechanism 26 described hereinabove with reference to a diagram. The difference is the configuration of the cam disk 33 and 33', respectively, in the second angular range α2. While the radius R in the embodiment according to FIG. 4 is constant in this section, it may also decrease slightly in the direction of rotation a according to FIG. 5. However, the degree of pitch of the range α2 is preferably less than the degree of pitch in the angle section α1. In particular, the decrease of the radius in the angular range α2 is so minimal that the spring means 35 are tensioned in any event, and thus the forceps tool 14 remains closed in order to firmly hold the vessel during the cutting phase. However, the gradient in the angular range α2 may act to decrease the force of actuation, in that the cam disk 33 aids the rotation of the shaft 36 in this angular range.

The instrument 10 according to the invention comprises an actuation gear mechanism 26 that—starting with the actuation of a manual actuation arrangement 24—performs two functions of a tool 11. To do so, the actuation gear mechanism 26 comprises a cam mechanism 31 as well as a gear segment mechanism 32. The circumference of the cam disk 33 of the cam mechanism 31 is—in a first section α1—a spiral curve for the generation of a stroke for closing the forceps tool 14, while the circumference of the cam disk 33—in a second, adjoining angular range α2—is on a circle. The tangential transition of the peripheral surface of the angle section α1 to the second angular range α2 can be viewed as the changeover point between courses of movement. As soon as the cam disk 33 having the circular section biases the spring means 35, there is no further movement at the output of the cam mechanism 31. This is achieved in that the cam follower member 34 and the axis 36 of the cam disk 33 are on the same line as the pulling means 27, so that there is no longer any counter-momentum from the cam disk 33 acting on the hand lever 23.

Preferably provided are two congruent cam disks 33, 34 that—together with the driving gear 41 and the segment gear 37, as well as the shaft 36—form a single-component injection-molded plastic part. This results in a low number of parts. The right and a left cam disk 33, 33' are configured for a symmetrical transmission of force. The installation space between the two cam disks 33, 33' can be used for a slide with a gear rack 40 for shifting the knife. Due to this interleaving of components, the entire required installation space is reduced, which allows the embodiment of a compact and ergonomic housing 21.

LIST OF REFERENCE SIGNS

| | |
|---|---|
| 10 | Instrument |
| 11 | Tool |
| 12, 13 | Branches |
| 14 | Forceps tool |
| 15 | Cutting tool |
| 16 | Knife |
| 17 | Hinge pin |
| 18 | Arrow |
| 19 | Cutting edge |
| 20 | Shaft |
| 21 | Housing |
| 22 | Handle |
| 23 | Hand lever |
| 24 | Manual actuation arrangement |
| 25 | Bearing point |
| 26 | Actuation gear mechanism |
| 27 | Pulling means |
| 28 | Pushing means |
| 29 | First output |
| 30 | Second output |
| 31 | Cam mechanism |
| 32 | Gear segment mechanism |
| 33, 33' | Cam disk |
| 34 | Cam follower member |
| 35 | Spring means |
| α1 | First angle section of the cam disk 33 |
| α2 | Second angular range |
| R | Radius of the cam disk 33 |
| 35 | Spring means |
| 36 | Shaft |
| 37 | Segment gear |
| 38, 39 | Sections of the segment gear |
| 40 | Gear rack |
| β1, β2 | Angular ranges of segment gear 37 |
| 41 | Gear |
| 42 | Gear segment |
| α0 | Starting position of shaft 36 |
| 43 | Transition section between α1 and α2 |
| 44 | First tooth of section 37 |
| α | Direction of rotation |

The invention claimed is:

1. An instrument (10) for performing surgical procedures on a patient, comprising:
   a tool (11) having at least two tool parts (12, 16) that are configured to be moved in a chronologically offset manner;
   an actuation gear mechanism (26) that includes a first output (29) for a first one of the tool parts (12) and a second output (30) for a second one of the tool parts (16);

a first transmission device (27) that is operatively connected to the first tool part (12) and the first output (29);

a second transmission device (28) that is operatively connected to the second tool part (16) and the second output (30);

wherein the actuation gear mechanism (26) includes a cam mechanism (31) that is operatively connected to the first output (29); and the actuation gear mechanism (26) includes a gear segment mechanism (32) that is operatively connected to the second output (30), wherein the cam mechanism (31) includes at least one cam disk (33) and at least one cam follower (34) that is in abutment with the at least one cam disk (33), and the at least one cam follower (34) is operatively connected to the first output (29).

2. The instrument according to claim 1, wherein the actuation gear mechanism (26) is connected to a manual actuation arrangement (24) on an input side of the actuation gear mechanism.

3. The instrument according to claim 1, wherein the tool (11) includes a forceps tool (14), and the first tool part (12) is a movable branch (12) of the forceps tool (14).

4. The instrument according to claim 1, wherein the tool (11) includes a cutting tool (15), and the second tool part (16) is a knife (16).

5. The instrument according to claim 1, wherein the first transmission device (27) is a pulling device and the second transmission device (28) is a pushing device.

6. The instrument according to claim 1, wherein the at least one cam disk (33) has at least one section ($\alpha2$) with a constant radius (R) that is not a function of an angle of rotation of the at least one cam disk and at least one other section ($\alpha1$) with a radius (R) that is a function of the angle of rotation of the at least one cam disk.

7. The instrument according to claim 1, wherein a spring (35) is arranged between the cam mechanism (31) and the first output (29).

8. The instrument according to claim 1, wherein the gear segment mechanism (32) includes a segment gear (37) and a gear rack (40) that is connected to the second output (30), and wherein the segment gear (37) has a peripheral section (38) without teeth and another peripheral section (39) provided with teeth that is configured to be brought into meshing engagement with the gear rack (40).

9. The instrument according to claim 1, wherein the gear segment mechanism (32) includes a segment gear (37) and a gear rack (40) that is connected to the second output (30), and wherein the at least one cam disk (33) and the segment gear (37) are connected to each other in a torque-proof manner.

10. The instrument according to claim 9, wherein the segment gear (37) and the at least one cam disk (33) are arranged relative to each other such that when the tool (11) is actuated, the segment gear (37) comes into engagement with the gear rack (40) only when an ascending section ($\alpha1$) of the at least one cam disk (33) has passed the at least one cam follower (34).

11. The instrument according to claim 1, wherein the gear segment mechanism (32) includes a segment gear (37) and a gear rack (40) that is connected to the second output (30), and wherein the actuation gear mechanism (26) comprises a transmission gearing for the conversion of a driving movement of a manual actuation arrangement (24) into a rotation of the at least one cam disk (33) and the segment gear (37).

12. The instrument according to claim 1, wherein the gear segment mechanism (32) includes a segment gear (37) and a gear rack (40) that is connected to the second output (30), and wherein the actuation gear mechanism (26) comprises a gear segment (42) that is in meshing engagement with a gear (41) that is connected in a driving manner to the at least one cam disk (33) and to the segment gear (37).

13. The instrument according to claim 12, wherein the gear segment (42) is connected to a pivot lever (23) that acts as a manual actuation arrangement (24).

14. The instrument according to claim 1, wherein the gear segment mechanism (32) includes a rotatable segment gear (37) and a gear rack (40) that is connected to the second output (30).

* * * * *